United States Patent [19]
Henderson et al.

[11] Patent Number: 5,861,376
[45] Date of Patent: *Jan. 19, 1999

[54] SYNTHETICALLY DERIVED PEPTIDE

[75] Inventors: James T. Henderson, Bradenton; Peter A. Vandenbergh, Sarasota, both of Fla.

[73] Assignee: Quest International Flavors & Food Ingredients Company, division of Indopco, Inc., Bridgewater, N.J.

[*] Notice: The term of this patent shall not extend beyond the expiration date of Pat. Nos. 5,231,165 and 5,173,297.

[21] Appl. No.: 30,911

[22] Filed: Mar. 15, 1993

Related U.S. Application Data

[60] Continuation-in-part of Ser. No. 882,715, May 14, 1992, Pat. No. 5,231,165, which is a division of Ser. No. 721,774, Jul. 1, 1991, Pat. No. 5,173,297.

[51] Int. Cl.$^6$ .............................. A61K 38/00; C07K 5/00; C07K 7/00
[52] U.S. Cl. ............................................... 514/12; 530/324
[58] Field of Search .............................. 514/12; 530/324

[56] References Cited

U.S. PATENT DOCUMENTS 5,173,297 12/1992 Vedamuthu et al. .

FOREIGN PATENT DOCUMENTS 9000558 of 1989 WIPO .
9000558 1/1990 WIPO .............................. C07H 21/04

OTHER PUBLICATIONS

Atherton, E., et al. "Solid phase peptide synthesis: a practical approach", IRL Press at Oxford University Press, Oxford, England, pp. 31–32 (1989).

Sarin, V.K., et al., Analytical Biochemistry, vol. 117, 147–157 (1981).

Kupke, T., Stevanovic, S., Sahl, H–G, and Gotz, F., J. Bacteriol. 174 5354–5361 (1992).

Schnell, N., et al., Nature 333 276–278 (1988).

Agricultural Food Research Center (AFRC) Yearly Report, Reading, Berkshire, England (1991).

Morris, S.L., et al., Biol. Chem. 259, 13590–13594 (1984).

Buchman, G. W., et al., J. Biol. Chem. 263 16260–16266 (1988).

Steen, M. T., et al., Appl. Environ. Microbiol. 57, 1181–1188 (1991).

Kaletta, C. et al., J. Bacterio. 171, 1597–1601 (1989).

Mulders, J. W. M., et al., J. Biochem. 201, 581–584 (1991).

Barber, M., et al., Experientia 44 266–270 (1988).

Liu and Hansen (Appl. Environ. Microbiol. 56, 2551–2558 (1990).

Chan, W. C., et al., FEBS Letters 252, 29–36 (1989).

Lian, L–Y., et al., Biochem. J. 283 413–420, (1992).

Mulders et al, Eur J. Biochem, vol. 201, pp. 581–584, 1991.

Buchman et al, J. Biol. Chem, vol. 263, No. 31, 5 Nov. 1988, pp. 16260–16266.

*Primary Examiner*—Avis M. Davenport
*Attorney, Agent, or Firm*—Ian C. McLeod

[57] ABSTRACT

A peptide (QSP-9124) was synthesized corresponding to the 34 residue sequence of a peptide precursor to the bacteriocin LL-2 produced by *Lactococcus lactis* LLA-2.0. The precursor to native bacteriocin LL-2 is extensively modified by post-translational mechanisms. Serine and threonine residues are dehydrated and lanthionine and methyl-lanthionine sulfur bridges are formed between cysteine and several of the dehydrated serine and threonine residues. The synthesized peptide has greater anti-bacterial action against *Listeria monocytogenes*, than did the native, post-translationally modified protein LL-2. Antibacterial activity against several beneficial food lactobacterial strains was absent, so that the peptide is of value as a food preservative against *L. monocytogenes*.

6 Claims, 2 Drawing Sheets

SYNTHETICALLY DERIVED PEPTIDE

CROSS-REFERENCE TO RELATED APPLICATION

The present invention is a continuation-in-part of application Ser. No. 07/882,715, filed May 14, 1992, now U.S. Pat. No. 5,231,165, which is a division of Ser No. 07/721,774, filed Jul. 1, 1991, now U.S. Pat. No. 5,173,297.

BACKGROUND OF THE INVENTION (1) Field of the Invention

The present invention relates to a synthetically derived peptide which is believed to be structurally related to a precursor peptide to a bacteriocin, preferably bacteriocin LL-2 produced by *Lactococcus lactis* subspecies lactis NRRL-B-18809. The peptide is referred to hereinafter as a "precursor peptide". In particular the present invention relates to a precursor peptide which is active against *Listeria monocytogenes* and inactive against Lactococcal food fermenting strains so that the precursor peptide is useful in fermented foods.

(2) Description of Related Art

Nisin and LL-2 are bacteriocins which differ from each other by a single amino acid in position 27. Nisin has a histidine (His) residue and LL-2 has an asparagine (Asn) residue. The compounds are characterized by a lanthionine bridge between residues 3 and 7.

In the preparation of precursor peptides, one approach is to chemically or thermally inactivate the pathway in the bacterium responsible for protein modification and then hope that the immunity genes also recognize the unmodified "immature" form of the peptide. The precursor peptide gene product would be self-lethal to the bacterium unless there is such immunity. This approach is time consuming to complete and may result in the intended modification but without a method for production due to lack of immunity. The applicability of this strategy is also less than certain, since the inactivation of a multi-enzyme pathway would be required, which might be difficult to obtain without losing viability of the bacterium due to a high level of mutations throughout the genome. Also, one or more of the enzymes responsible for post-translational modification of the precursor peptide to produce the bacteriocin might also be essential to cell viability. Further a lack of information exists regarding the generality of side chain dehydration and lanthionine formation in cellular proteins. Also, the bacterial strain might have developed specialized transport mechanisms which serve to keep unmodified bacteriocin inside and modified bacteriocin outside of the cell. To maintain a system of modification enzymes and then allow unmodified bacteriocin precursor peptide to escape the confines of the cell is contradictory.

A second approach is to clone the DNA pre-protein sequence into a foreign bacterium lacking the enzymes for post-translational modification and to induce expression. Quantities of pre-protein could be obtained by purification of the growth medium. Again, the same problems with immunity and transport in the modified bacterial strains may apply. Although this alternative is attractive, a much greater effort is required with a much less chance at successfully isolating the desired product.

Keeping in mind the difficulty of producing a bacteriocin precursor peptide by microbiological methods, undertaking of such a project would require the expectation that study of the precursor peptide would be interesting in some way. If the prediction were made that the immature peptide is active, one would reasonably ask why does the bacterium take on the energy cost to modify an already functional peptide. Organisms keep notably conservative energy budgets and do not generally invest energy in frivolous protein modification. The possibility exists that modifications evolved in order to provide an evolutionary advantage such as to prolong the lifetime of the active state by evading degrading enzymes or to maintain activity in a reducing or dehydrating environment. Lanthionine bridging is stable under many conditions which disrupt disulfide bridging. However, the prediction could reasonably be made that if a particular strain had developed immunity to the post-translationally modified form of the protein, such immunity might not transfer to the precursor peptide. The producer bacterium, on the other hand, must at one time have had immunity to the precursor peptide assuming that the post-translationally modified form evolved over time from the precursor peptide.

Post-translational modification of native LL-2 may involve three or more enzymes, as was recently proposed for epidermin (Kupke, T., Stevanovic, S., Sahl, H-G, and Gotz, F., J. Bacteriol. 174 5354–5361 (1992)). Epidermin contains two lanthionine bridged rings and one methyl-lanthionine bridged ring (Schnell, N., Entian, K-D., Schneider, U., Gotz, F., Zahner, H., Kellner, R., and Jung, G, Nature 333 276–278 (1988)) similar to the modifications present in mature LL-2.

Published studies have communicated a belief that post-translational modifications are necessary for the activity of nisin-like proteins. This is no more apparent than in the AFRC (Agricultural Food Research Center, Reading, Berkshire, England) yearly report of 1991. The authors used a "gene probe designed from the predicted amino acid sequence of prenisin to clone the nisin biosynthetic region of a *Lactococcus lactis* nisin producer." Instead of using this sequence to produce the nisin peptide precursor directly, they created a system to mature and express the nisin precursor peptide and variants by inactivating the nisA nisin coding gene. Then the authors introduced a plasmid carrying the nisA gene or a variant to this system in order to study the mature protein and variants with novel properties. What the authors failed to investigate was the prenisin gene product itself for anti-bacterial activity. Perhaps the nisin secretion mechanism is inoperable for the precursor peptide sequences. It would be to the advantage of the bacterial strain, if the strain were extensively involved in post-translationally modifying nisin for the export mechanism not to recognize and secrete the unmodified precursor.

Morris, et al. (Morris, S. L., Walsh, R. C., and Hansen, J. N., Biol. Chem. 259, 13590–13594, (1984)) state "The activity of nisin is associated with dehydroalanine residues which could react with sulfhydryl groups". The twin observations were that nisin produces (1) inhibition of spore outgrowth and (2) inactivation of membrane sulfhydryl groups of germinated *Bacillus cereus* spores. The likelihood that nisin has "evolved the specific capability to inactivate membrane sulfhydryl groups of this (germinated *B. cereus* spores) type" is compared to the high specificity of "natural" antibiotic action.

Hansen (WO 90/00558 to Norman J. Hansen, 30 Jun., 1989) cloned the subtilin precursor gene into M13 along with a promotor (TATAAT) and ribosomal binding site (RBS). Similarly a nisin precursor sequence was cloned into M13mp18 for sequencing. In both cases, presence of a particular leader sequence between the RBS and the peptide sequence was claimed necessary to direct post-translational modification. Expression of the unmodified precursor peptide is discussed (hypothetically) in terms of excising the particular leader sequence responsible for post-translational modification. No use of the precursor protein is disclosed. In fact, whether the hypothetical experiment would work at all depends on the factors discussed previously including immunity to the precursor peptide, and detection of antibacterial activity.

The precursor peptide to nisin and LL-2 both contain a 23 amino acid residue leader region in addition to the 34 amino acid structural region (Buchman, G. W., Banerjee, S., and Hansen, J. N., J. Biol. Chem. 263 16260–16266, (1988)). The nisin gene is part of a polycistronic operon which may also contain genes for post-translational processing of the precursor peptide (Steen, M. T., Chung, Y. G., and Hansen, J. N., Appl. Environ. Microbiol. 57, 1181–1188, (1991)). The leader region and amino terminal end of nisin have considerable homology to epidermin (Kaletta, C. and Entian, K-D., J. Bacterio. 171, 1597–1601 (1989)). The leader sequence cleavage point (proline-arginine isoleucine) is the same in both precursor peptides. The first 5 member ring and the second 4 member ring are nearly identical except that $Ile^4$, $Dha^5$ and $Leu^6$ in nisin are $Lys^4$, $Phe^5$ and $Ile^6$ in epidermin. If $Dha^5$ is a nucleophile important to biological activity, then $Phe^5$ must play this role in epidermin. The C-terminal ends of epidermin and nisin are very different, showing no significant homology and having different numbers and types of bridges.

The DNA sequence of LL-2 differs from nisin in that the codon for the 27th amino acid, His is changed to Asn by natural mutation. The native protein encoded with this mutation (with post-translational modification and containing the 27 Asn mutation) has been described. (Mulders, J. W. M., Boerrigter, I. J., Rollema, H. S., Siezen, R. J., and de Vos, W. M., Eur. J. Biochem. 201, 581–584, (1991)). The DNA sequence was used to determine the protein sequence since only small parts of the protein sequence were determinable directly due to post-translational modification.

The structure of nisin had been determined prior to obtaining the gene sequence (Barber, M., et al., Experientia 44 266–270 (1988)), but a single ambiguity remained. The sole lanthionine bridge between residues 3 and 7 could have been formed by a cysteine either preceding a serine or following a serine in the DNA sequence. Prediction of an unambiguous precursor peptide from this data is not possible. By contrast, occurrences of methyl-lanthionine are unambiguously determinable since the portion of the molecule with the methyl group arises from the threonine portion of a cysteine, threonine pair.

Liu and Hansen (Appl. Environ. Microbiol. 56, 2551–2558 (1990)) used mercaptans or elevated pH to inactivate nisin. The cause of inactivation was presumed to be a chemical reaction between nucleophiles and dehydro residues, implying that dehydro residues are required for activity. The proposed chemical reaction was that the dehydro residues of nisin act as electrophilic Michael acceptors toward nucleophiles in the target. Treatment with cyanogen bromide resulted in two products. Each purified fragment was active but at a 10 fold diminished specific activity. The biological activity measured was the inhibition of *B. cereus* T spores in the elongated state. This measure of activity may not correlate well with other measurements of activity such as bacteriocidal activity.

Chan et al (Chan, W. C., Bycroft, B. W., Lian, L-Y, and Roberts, G. C. K., FEBS Letters 252, 29–36 (1989)) report an inactive degradation product in which $dehydroalanine^{33}$, $lysine^{34}$ and $dehydroalanine^5$ ($DHA^5$) are missing. The degradative removal of $DHA^5$ causes an opening of the first ring structure. The loss of $dehydroalanine^{33}$ and $lysine^{34}$ alone ($nisin^{1-32}$) did not cause inactivation. The biological activity discussed in this reference is measured by minimum inhibitory concentration (MIC, µg/ml) against several gram positive and a single gram negative bacterium. Subsequent NMR studies (Lian, L-Y., Chan, W. C., Morley, S. D., Roberts, G. C. K., Bycroft, B. W., and Jackson, D., Biochem. J. 283 413–420, (1992)) of the same degradation product showed increased flexibility and lack of well defined structure in the region of $DHA^5$ compared to nisin. This was interpreted as an indication of increased conformational flexibility because of removal of $DHA^5$ and opening of the lanthionine defined ring. The hypothesis was drawn that dehydro residues in nisin play an important part in the mechanism of nisin antibiotic action. Dehydro residues were hypothesized to provide antibiotic action by reacting with a specific cellular nucleophile target.

OBJECTS

It is therefore an object of the present invention to provide a synthetically derived peptide which is a bacteriocin precursor peptide and which is active against *Listeria monocytogenes* and which is inactive against food fermenting Lactococcal strains. Further, it is an object of the present invention to provide a method for inhibiting *L. monocytogenes* using the peptide. These and other objects will become increasingly apparent by reference to the following description and the drawing.

DESCRIPTION OF PREFERRED EMBODIMENTS

Figure 1:
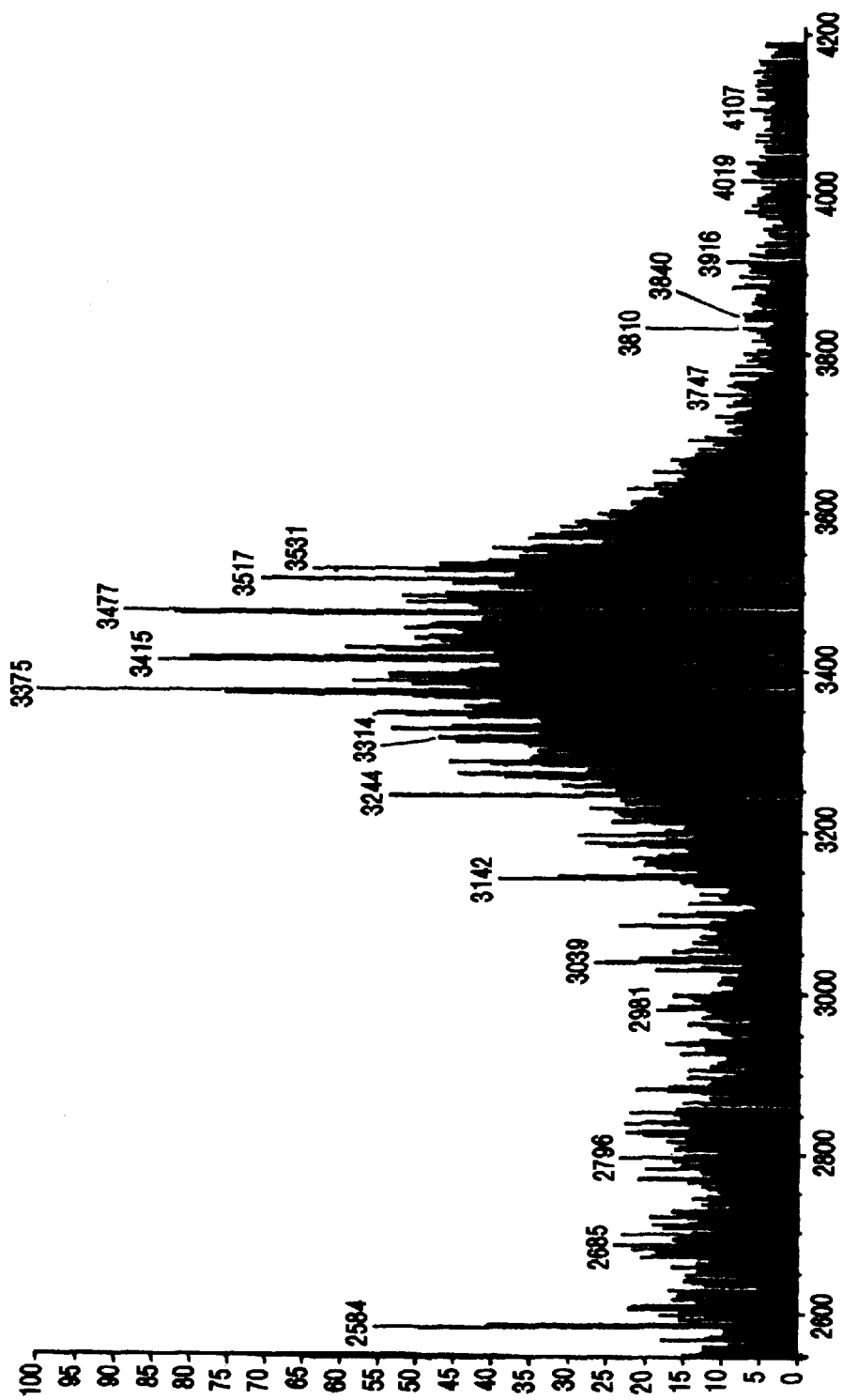
FIG. 1 is a mass spectrum of the synthetically derived peptide QSP-9124 using a vg analytical 2432-5E high yield mass spectrometer operating at Vacc=8 kv. The matrix was m-nitrobenzyl alcohol with 5% acetic acid solvent.

The present invention relates to a synthetically derived peptide which comprises:

Ile Thr Ser Ile Ser Leu Cys Thr Pro Gly Cys
                    5                    10
Lys Thr Gly Ala Leu Met Gly Cys Asn Met Lys
               15                    20
Thr Ala Thr Cys Xaa Cys Ser Ile His Val Ser
               25                30
Lys, which is also known as QSP-9124 when Xaa is Asn, as set forth in SEQ ID NO. 1, wherein Xaa is selected from the group consisting of Asn and His.

Further, the present invention relates to a method for inhibiting Listeria sp in a medium in which the Listeria sp grows which comprises: providing an effective amount of a synthetically derived peptide having the formula:

Ile Thr Ser Ile Ser Leu Cys Thr Pro Gly Cys
                    5                    10
Lys Thr Gly Ala Leu Met Gly Cys Asn Met Lys
               15                    20
Thr Ala Thr Cys Xaa Cys Ser Ile His Val Ser
               25                30
Lys, which is also known as QSP-9124 when Xaa is Asn, as set forth in SEQ ID NO.1 in the medium, wherein Xaa is selected from the group consisting of Asn and His.

Synthesis of the precursor peptide was used to evaluate the peptide in the absence of modifications of LL-2, wherein Xaa is His, by the bacterium. This approach particularly was used to isolate the precursor peptide in substantial amounts and purity and to determine the antibacterial activity of the precursor peptide.

The synthetically derived peptide QSP-9124 particularly differs from native LL-2 in that dehydro residues and lanthionine bridges are not present. There are 5 cysteine residues, 5 threonine residues and 3 serine residues present. In native LL-2, these residues are produced by dehydration and sulfur bridge formation or both. These modifications have the effect of modifying the local polarity of synthetic LL-2 by the presence of hydroxyl groups from the serine and threonine residues and by the presence of free sulfhydryl groups in the 5 cysteine residues in the synthetic precursor peptide. The lack of intrachain sulfur crosslinks in the synthetic precursor peptide LL-2 has the effect of modifying the tertiary structure to allow freedom of movement not possible in the native bacteriocin LL-2.

The precursor peptide is preferably used in amounts between about 10 and 500 AU/gram of the food. An AU is the least detection of the peptide which will provide activity as discussed hereinafter. The foods are particularly dairy products, such as yogurt, cheese, Cottage cheese, ice cream and the like.

Native LL-2 can be obtained from *Lactococcus lactis* NRRL-B-18809. It is deposited at the Northern Regional Research Laboratory in Peoria, Ill. and is available on request. The native bacteriocin is described in U.S. Pat. No. 5,173,297 assigned to a common assignee.

EXAMPLE 1

Materials and Preparation

The peptide QSP-9124 was synthesized by the stepwise addition of base labile FMOC amino protected amino acids to a support consisting of p-benzyloxybenzyl alcohol (Wang, S. S., JACS 95 1328 (1973)) resin with lysine pre-attached. FMOC is N$\alpha$-9-fluorenylmethoxycarbonyl. The extent of lysine attachment was 0.1 millimoles and therefore set the maximum yield of synthesized peptide to the same amount. Activation of the incoming amino acid was done using the reagent, benzotriazolyloxy-trisdimethylaminophosphonium hexaf luorophosphate (BOP), which was premixed in the vial containing the amino acid. Numerous references exist to the FMOC method of peptide synthesis; one of the better known is "Solid phase peptide synthesis: a practical approach", E. Atherton and R. C. Sheppard, IRL Press at Oxford University Press, Oxford, England, pages 31–32 (1989). Acid labile protecting groups were used to prevent unwanted side chain reactions for several amino acids. These amino acids include serine (t-butyl), threonine (t-butyl), cysteine (trityl), asparagine (trityl), lysine (BOC) and histidine (trityl).

The reaction was judged for completeness in each cycle of addition by using a ninhydrin monitoring procedure (Sarin, V. K., et al., Analytical Biochemistry, Vol. 117, 147–157 (1981)) to determine free amino (ninhydrin reactive) content of a weighed amount of resin.

Resin-bound QSP-9124 was cleaved from the resin using either trifluoroacetic acid or trifluoroacetic acid with trifluoromethanesulfonic acid. Protecting agents were added to scavenge byproducts from the cleavage reaction. Protecting agents were chosen from a group consisting of phenol, anisole, thioanisole and ethanedithiol. The cleavage reaction was done under nitrogen, at room temperature for 25–90 minutes.

Cleaved peptide was separated from resin by filtration (0.22 $\mu$m filter) and partial purification was obtained by precipitation using diethyl ether (Et$_2$O). Precipitated protein was dried and reconstituted in trifluoroacetic/acetic acid (1:4). Activity against *P. pentosaceus* was confirmed by spotting reconstituted synthetic precursor peptide on an indicator lawn. Purified synthetic precursor peptide was then obtained using semi-preparative HPLC techniques with a 10 cm octadecyl silane column (Vydac, Hisperia, Calif.). Activity in the HPLC fractions was determined by spotting 5 $\mu$l aliquots from each HPLC fraction onto an FBB-63C indicator lawn. Active HPLC fractions were obtained in the region of 26.5–28 minutes elution. Specific activity of the main active fraction of each cleavage reaction ranged from 850 AU/mg to 9600 AU/mg.

Bacteriostatic activity of the purified synthetic precursor peptide preparation was determined by spotting 5 $\mu$l of a serial twofold dilution series onto MRS plates overlaid with semisolid agar seeded with *Pediococcus pentosaceus* FBB-63C indicator cells. Activity against *Listeria monocytogenes* was determined similarly except TSA agar was overlaid with semisolid TSA seeded with *Listeria monocytogenes*. After the overlay had solidified, the plates were dried for 15 minutes and were spotted with 5 $\mu$l of the precursor peptide preparation. The plates were incubated overnight at 35° C. The next day, plates were examined for zones of inhibition. One activity unit "AU" is defined as the reciprocal of the highest dilution yielding a definite inhibition zone on the indicator lawn.

RESULTS

Resin was removed manually from the reaction vessel after each cycle to determine completeness of coupling. In two instances namely the addition of Lys$_2$ to Cys$_{11}$ and the addition of Thr$_{13}$ to Lys$_{12}$, a second coupling was judged necessary due to a high free amino group concentration. After coupling a second time using similar reagents, 98% or better conversion was obtained. In a third instance, the addition of Cys$_{11}$ to Gly$_{10}$, conversion was only 96% after the second coupling. In all three of these steps, acetic anhydride was added to the reaction vessel after the second coupling to reduce unreacted amino groups to less than 0.5% before proceeding to the next step. By calculating the yield after each step without including acetylated amino groups the overall yield of peptide was 78.1% and the average conversion was 99.3% for all steps. The results are shown in Table 1.

TABLE 1

QSP 9124 [a]

| | | | % Conversion | |
|---|---|---|---|---|
| Cycle | Residue | Step | Overall | Peptide |
| 1 | Ser | 33 | 99.5 | 99.5 | 99.5 |
| 2 | Val | 32 | 99.5 | 99.3 | 99.3 |
| 3 | His | 31 | 99.5 | 98.8 | 98.8 |
| 4 | Ile | 30 | 96.6 | 97.6 | 97.6 |
| 5 | Ser | 29 | 99.7 | 97.3 | 97.3 |
| 6 | Cys | 28 | 99.5 | 97.0 | 97.0 |
| 7 | Asn | 27 | 99.9 | 96.9 | 96.9 |
| 8 | Cys | 26 | 99.8 | 96.7 | 96.7 |
| 9 | Thr | 25 | 99.6 | 96.3 | 96.3 |
| 10 | Ala | 24 | 99.9 | 96.2 | 96.2 |
| 11 | Thr | 23 | 99.8 | 96.0 | 96.0 |
| 12 | Lys | 22 | 99.6 | 95.6 | 95.6 |
| 13 | Met | 21 | 99.6 | 95.2 | 95.2 |

TABLE 1-continued

QSP 9124 [a]

| Cycle | | umol/g | % conv. | | | |
|---|---|---|---|---|---|---|
| 14 | Asn | 20 | 99.5 | 95.1 | 95.1 | |
| 15 | Cys | 19 | 99.9 | 95.0 | 95.0 | |
| 16 | Gly | 18 | 99.9 | 94.8 | 94.8 | |
| 17 | Met | 17 | 99.6 | 94.4 | 94.4 | |
| 18 | Leu | 16 | 99.8 | 94.2 | 94.2 | |
| 19 | Ala | 15 | 99.4 | 93.7 | 93.7 | |
| 20 | Gly | 14 | 99.4 | 93.1 | 93.1 | |
| 21 | Thr | 13 | 96.1 | 91.3 | 93.0 | |
| 22 | Lys | 12 | 96.3 | 89.8 | 92.6 | |
| 23 | Cys | 11 | 95.9 | 86.1 | 92.2 | |
| 24 | Gly | 10 | 99.5 | 85.9 | 82.0 | |
| 25 | Pro | 9 | 99.4 | 85.4 | 91.5 | |
| 26 | Thr | 8 | 99.2 | 84.7 | 90.7 | |
| 27 | Cys | 7 | 99.2 | 84.0 | 90.0 | |
| 28 | Leu | 6 | 96.9 | 83.1 | 89.1 | |
| 29 | Ser | 5 | 99.3 | 82.5 | 88.4 | |
| 30 | Ile | 4 | 96.6 | 81.4 | 87.2 | |
| 31 | Ser | 3 | 96.7 | 80.3 | 86.0 | |
| 32 | Thr | 2 | 98.8 | 79.4 | 85.1 | |
| 33 | Ile | 1 | 96.4 | 78.1 | 83.7 | |
| Average: | | | 99.3 | 91.4 | 83.5 | |

| | First couple | | Second couple | | Acetylation | |
|---|---|---|---|---|---|---|
| Cycle | umol/g | % conv. | umol/g | % conv. | umol/g | % conv. |
| 1 | 0.4 | 99.8 | | | | |
| 2 | 1.2 | 99.5 | | | | |
| 3 | 1.3 | 99.5 | | | | |
| 4 | 2.9 | 98.8 | | | | |
| 5 | 0.7 | 99.7 | | | | |
| 6 | 0.9 | 99.6 | | | | |
| 7 | 0.3 | 99.9 | | | | |
| 8 | 0.4 | 99.8 | | | | |
| 9 | 0.9 | 99.6 | | | | |
| 10 | 0.3 | 99.9 | | | | |
| 11 | 0.5 | 99.8 | | | | |
| 12 | 1.0 | 99.6 | | | | |
| 13 | 1.0 | 99.6 | | | | |
| 14 | 0.4 | 99.8 | | | | |
| 15 | 0.3 | 99.9 | | | | |
| 16 | 0.3 | 99.9 | | | | |
| 17 | 1.0 | 99.6 | | | | |
| 18 | 0.6 | 99.6 | | | | |
| 19 | 1.4 | 99.4 | | | | |
| 20 | 1.4 | 99.4 | | | | |
| 21 | 8.2 | 96.6 | 4.7 | 96.1 | 0.4 | 99.8 |
| 22 | 8.0 | 96.7 | 4.2 | 98.3 | 0.9 | 99.6 |
| 23 | 13.9 | 94.3 | 10.0 | 95.9 | 1.0 | 99.6 |
| 24 | 0.5 | 99.8 | | | | |
| 25 | 1.5 | 99.4 | | | | |
| 26 | 2.0 | 99.2 | | | | |
| 27 | 1.9 | 99.2 | | | | |
| 28 | 2.6 | 96.9 | | | | |
| 29 | 1.7 | 93.3 | | | | |
| 30 | 3.4 | 96.6 | | | | |
| 31 | 3.2 | 96.7 | | | | |
| 32 | 2.8 | 96.8 | | | | |
| 33 | 3.8 | 96.4 | | | | |
| Average: | | 99.1 | | | | |

[a] Resin type: Lys 0.1 mmol;
Resin weight: 0.1314 g;
Ninhyd. sites: 243 umol/g;
Total sites: 0.03193 umol and 3.2E-05 mmol;
Calc. sites: 761 umol/g and 0.1 mmol total The calculated molecular weight of QSP-9124 is 3476 Daltons and the calculated pI is 8.86 when cysteines are in the sulfhydryl form. The amino acid composition contains no aromatic residues besides one histidine residue and no acidic sidechains. The basic pI is therefore a result of 3 lysine residues. The presence of 4 serine and 5 threonine residues is uncommon in a peptide of this size. The native bacteriocin LL-2 has a calculated pI of 10.7 and a molecular weight of 3314 Da. The molecular weight difference between synthetic LL-2 and native LL-2 reflects a conversion of 4 serine and 5 threonine residues to the dehydro form. Formation of lanthionine type bridging results in no net weight change. Amino acid analysis of crude cleavage products of QSP-9124 before HPLC purification gave the results shown in Table 2.

TABLE 2

Amino acid composition results for synthetic precursor peptide LL-2.

| Amino Acid | Expected | QSP-9124 |
|---|---|---|
| Asp | 2 | 2.7 |
| Ser | 4 | 3.5 |
| Gly | 3 | 3.4 |
| His | 1 | 1.1 |
| Thr | 5 | 4.4 |
| Al | 2 | 2.7 |
| Pro | 1 | 0.6 |
| Val | 1 | 1.6 |
| Met | 2 | 2.4 |
| Cys | 5 | 3.2 |
| Ile | 3 | 2.8 |
| Leu | 2 | 2.3 |
| Lys | 3 | 3.3 |
| TOTAL | 34 | 34 |

EXAMPLE 2

The activity spectrum of the synthetic precursor peptide QSP-9124 included *Listeria monocytogenes* LM04. This strain is not inhibited by crude native bacteriocin LL-2. The peptide also inhibits *Pediococcus pentosaceus*. Titer against *Listeria monocytogenes* of a 2 mg/ml solution was determined by spot assay to be 6400 AU/ml which is a significant inhibition. An activity spectrum was determined against several gram positive and gram negative strains as shown in Table 3.

TABLE 3

Activity spectrum of synthetic precursor peptide QSP-9124 compared to crude medium containing native bacteriocin LL-2.

| Strain | native LL-2 crude | QSP-9124 (C3-27.5) 2 mg/ml |
|---|---|---|
| *Pediococcus pentosaceus* FBB-63C | 1600 AU/ml | 800 AU/ml |
| *Listeria monocytogenes* LM04 | no inhibition | 6400 AU/ml |
| *Lactobacillus casei* 842 | slight inhibition | slight inhibition |
| *Staphylococcus aureus* Z88 | no inhibition | no inhibition |
| Salmonella | no inhibition | no inhibition |
| *Pseudomonas fragii* | no inhibition | no inhibition |
| *Escherichia coli* | no inhibition | no inhibition |
| *Lactococcus lactis* LLA 2.0 | no inhibition | no inhibition |

EXAMPLE 3

A mass spectrum of HPLC purified synthetic QSP-9124 (C3-27.5) confirmed the presence of a 3477 Dalton moiety as shown in FIG. 1. This is the calculated molecular weight of the appropriate sequence in the absence of disulfide bonding (all five cysteine sulfhydryl groups in the reduced state).

The amino acid analysis of the synthetic precursor peptide (QSP-9124) shows good agreement with composition predicted by the sequence with the exception of cysteine residues. Cysteine residues are at times difficult to determine by conventional amino acid analysis unless separately derivatized. The derivatization experiment was not done on any samples of QSP-9124. Instead, mass spectral analysis was done in a non-reducing matrix in order to preserve the redox state of individual cysteine residues. Mass spectral analysis indicated that the overall composition was in agreement with the intended composition and that all five cysteine residues were in the reduced state (i.e. no disulfide bonds are present in the synthetic preprotein). A predominant mass-ion at 3375 m/z is probably due to the deletion of a cysteine residue which might have arisen from incomplete coupling.

The synthetically derived peptide QSP-9124 duplicates the peptide obtained by translation of the DNA sequence which codes for the anti-bacterial protein produced by the *L. lactis* LLA-2.0 (NRRL-B-18089 as described in Ser. No. 07/721,774) bacterium. Whether this peptide exists in quantity in the cell is unknown and depends on whether the post-translational modification operates as concerted reactions with ribosomal production of peptide. The native peptide has never been detected as a secreted product. The synthetic peptide is useful because it exhibits activity against *Listeria monocytogenes* where such activity is lacking in the crude bacteriocin LL-2.

The activity spectrum shows that QSP-9124 does not inhibit *Lactococcus lactis* LLA 2.0 which indicates that immunity of LLA 2.0 to the peptide is probably present. Thus the LLA 2.0 strain could be made to produce QSP-9124 singly or in combination with LL-2. The conclusion can be drawn from the data presented here that the post-translational modifications which distinguish LL-2 from the LL-2 precursor are not essential to provide a peptide with anti-bacterial activity from this sequence. The intrachain crosslinks provided by lanthionine and methyl-lanthionine bridging are absent in the precursor peptide and so if there is a preferred folding, it is likely different from that of LL-2. Mass spectral data indicates that all five cysteine residues exist in the reduced form suggesting the absence of any intrachain crosslinks.

Since QSP-9124 without dehydroalanine residues and since no dehydroalanine residues are detected as spontaneously arising during purification, the mechanism proposed by Morris et al described above must not be a complete explanation of anti-bacterial activity.

EXAMPLE 4

The modification of Xaa to His[27] produces similar results since nisin is an active natural antibiotic.

*Listeria monocytogenes* strain LM04, containing pNZ123 to confer chloramphenicol resistance, was grown to an OD600 between 0.2 and 0.3. The strain was then serially diluted 1/10000 before use.

The synthetic peptide of Example 1 was titered against *Pediococcus pentosaceus* strain FBB63C and *L. monocyto-genes* strain LM04. The titer against FBB63C was <200 AU/gram and the titer against LM04 was 3200 AU/gram.

Native LL2 powder was used as the control. A 20% solution was made and titered against *Pediococcus pentosaceus* strain FBB63C and *L. monocytogenes* strain LM04. The titer against FBB63C was 6400 AU/gram. There was no titer against LM04.

The following experiment was set up for the synthetic peptide:

| Volume Skim Milk | Volume LL2 | Vol. Cells | Titer |
| --- | --- | --- | --- |
| 5.0 ml | 0.5 ml | 0.2 ml | 320 AU/g |
| 5.0 ml | 0.25 ml | 0.2 ml | 160 AU/g |
| 5.0 ml | 0 ml | 0.2 ml | 0 AU/g |

The following experiment was set up for the native LL2 product.

| Volume Skim Milk | Volume LL2 | Vol. Cells | Titer |
| --- | --- | --- | --- |
| 5.0 ml | 0.5 ml | 0.2 ml | 640 AU/g |
| 5.0 ml | 0.25 ml | 0.2 ml | 320 AU/g |
| 5.0 ml | 0.125 ml | 0.2 ml | 160 AU/g |
| 5.0 ml | 0 ml | 0.2 ml | 0 AU/g |

Sterile deionized water was used to adjust all volumes in both sets of experiments to the same level. The volume of cells used was the amount necessary to add 1000 cfu's/gram to the milk.

Counts were performed at Day 0, Day 1, Day 7. The media for counting was BHI Cm10.

Figure 2:
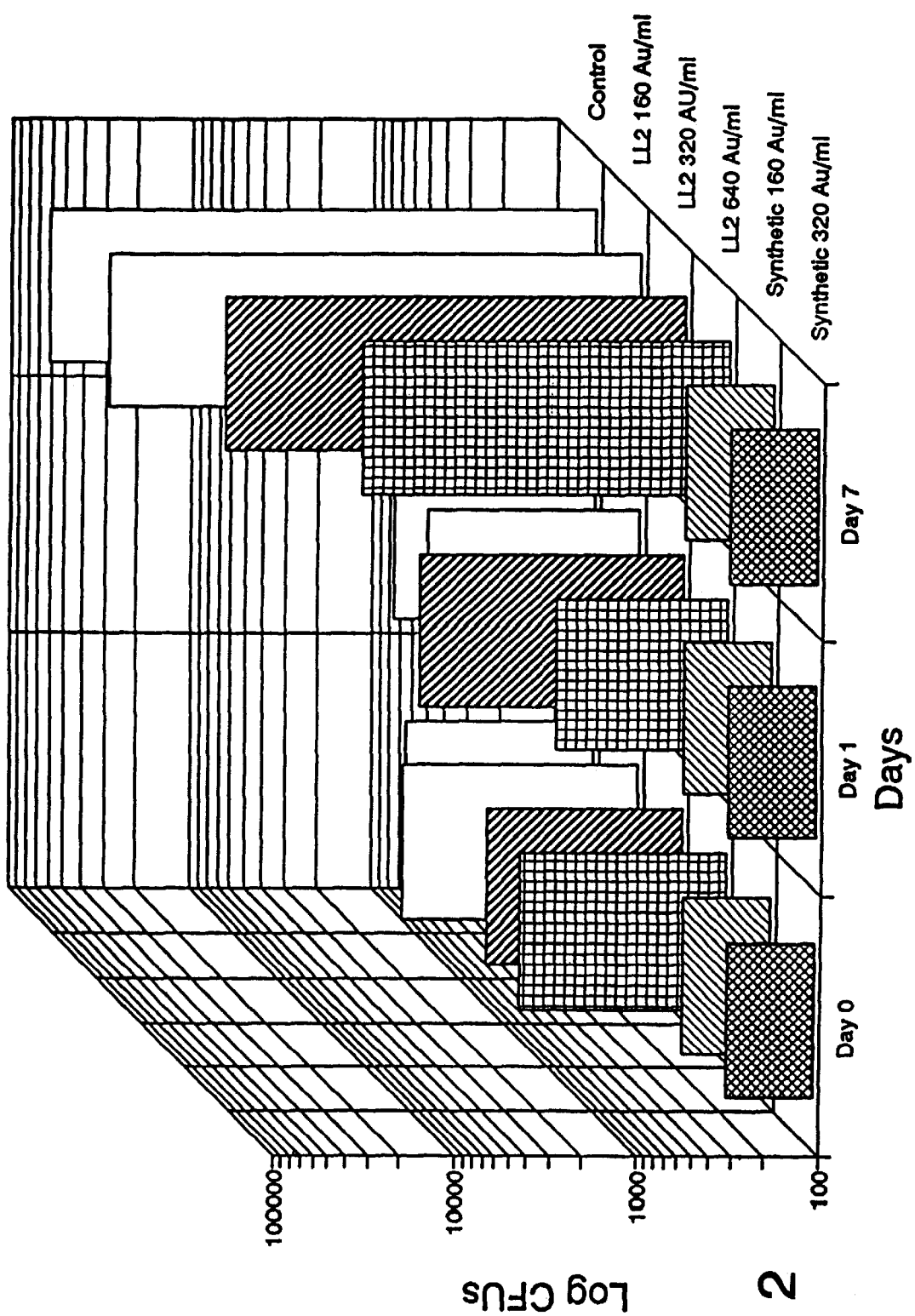
FIG. 2 is a graph showing the results with the synthetic peptide versus the native peptide LL-2 against *Listeria monocytogenes*.

The results are shown in Table 4 and FIG. 2.

TABLE 4

Activity of synthetic Peptide Versus Native LL-2 on *Listeria monocytogenes* in Skim Milk

| | Natural LL-2 | | | Synthetic LL-2 | | Control |
| --- | --- | --- | --- | --- | --- | --- |
| | 160 Au/ml | 320 Au/ml | 640 Au/ml | 160 Au/ml | 320 Au/ml | No Additive |
| Day 0 | 1920* | 1160 | 1340 | 300 | 300 | 1070 |
| Day 1 | 1420 | 2730 | 850 | 300 | 300 | 1240 |
| Day 7 | 81500 | 32500 | 10100 | 300 | 300 | 98500 |

*CFU/ml

The data clearly shows that the synthetic LL-2 is clearly superior to the native peptide LL-2 in inhibiting *Listeria monocytogenes* in milk as the food. Other foods, particularly those containing milk or milk products, can be provided with the synthetic polypeptide with equivalent results. It is intended that the foregoing description be only illustrative of the present invention and that the present invention be limited only by the hereinafter appended claims.

I claim:

1. A method for inhibiting Listeria sp in a medium in which the Listeria sp is present which comprises:

providing an effective amount of a synthetic peptide having the formula:

```
Ile  Thr  Ser  Ile  Ser  Leu  Cys  Thr  Pro  Gly  Cys
                         5                        10
Lys  Thr  Gly  Ala  Leu  Met  Gly  Cys  Asn  Met  Lys
                    15                  20
Thr  Ala  Thr  Cys  Xaa  Cys  Ser  Ile  His  Val  Ser
               25                  30
Lys
``` as set forth in SEQ ID NO. 1 wherein Xaa is selected from the group consisting of His and Asn in the medium containing the Listeria sp.

2. The method of claim 1 wherein the medium is a food.

3. The method of claim 2 wherein the food is a dairy product.

4. The method of claim 2 wherein between about 10 and 500 AU per gram of the food is used.

5. The method of claim 1 wherein Xaa is Asn.

6. The method of claim 1 wherein Xaa is His.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 34 Amino Acids
        ( B ) TYPE: Amino Acid
        ( D ) TOPOLOGY: Linear ( i i ) MOLECULE TYPE: Peptide ( x i ) SEQUENCE DESCRIPTION: SEQ ID NO:1:

```
Ile  Thr  Ser  Ile  Ser  Leu  Cys  Thr  Pro  Gly  Cys  Lys
                         5                        10
Thr  Gly  Ala  Leu  Met  Gly  Cys  Asn  Met  Lys  Thr  Ala
               15                  20
Thr  Cys  Xaa  Cys  Ser  Ile  His  Val  Ser  Lys
25                            30
```

( 2 ) INFORMATION FOR SEQ ID NO:2:

( i ) SEQUENCE CHARACTERISTICS:
        ( A ) LENGTH: 34 Amino Acids
        ( B ) TYPE: Amino Acid
        ( D ) TOPOLOGY: Linear ( i i ) MOLECULE TYPE: Peptide ( x i ) SEQUENCE DESCRIPTION: SEQ ID NO:2:

```
Ile  Thr  Ser  Ile  Ser  Leu  Cys  Thr  Pro  Gly  Cys  Lys
                         5                        10
Thr  Gly  Ala  Leu  Met  Gly  Cys  Asn  Met  Lys  Thr  Ala
               15                  20
Thr  Cys  Asn  Cys  Ser  Ile  His  Val  Ser  Lys
25                            30
```